United States Patent [19]

Honig et al.

[11] Patent Number: 4,791,310

[45] Date of Patent: Dec. 13, 1988

[54] FLUORESCENCE MICROSCOPY

[75] Inventors: Arnold Honig, Oran; James E. Smith, Camillus, both of N.Y.

[73] Assignee: Syracuse University, Syracuse, N.Y.

[21] Appl. No.: 914,367

[22] Filed: Oct. 2, 1986

[51] Int. Cl.⁴ .................................. G01N 21/31
[52] U.S. Cl. ........................ 250/458.1; 250/461.2
[58] Field of Search ............ 250/461.1, 461.2, 458.1, 250/271; 356/317, 318, 417; 283/93

[56] References Cited

U.S. PATENT DOCUMENTS

| | | | |
|---|---|---|---|
| 4,006,360 | 2/1977 | Mueller | 250/461.2 |
| 4,058,732 | 11/1977 | Wieder | 250/461.1 |
| 4,236,071 | 11/1980 | Chimenti | 250/461.1 |
| 4,573,796 | 3/1986 | Martin et al. | 250/461.2 |
| 4,626,693 | 12/1986 | Hirschfeld | 250/461.1 |

FOREIGN PATENT DOCUMENTS 2095822 10/1982 United Kingdom ............... 250/271

*Primary Examiner*—Carolyn E. Fields
*Assistant Examiner*—John A. Miller
*Attorney, Agent, or Firm*—Wall and Roehrig

[57] ABSTRACT

A multi-chronal fluorescence imaging technique for spatial differentiation and correlation of a plurality of separate sample components tagged with site specific dyes is described. The dyes have decay times that are widely separated and vary by approximately a factor of ten from one dye to the next. These are added to the sample and are excited with a short pulse of ultraviolet light. Between the sample and a detector is placed an adjustable shutter or gate which is opened and closed at predetermined intervals so that the detector can see the approximate maximum intensity output of each dye in a shown ordered sequence without significant interference from the other dyes.

18 Claims, 2 Drawing Sheets

FLUORESCENCE MICROSCOPY

BACKGROUND OF THE INVENTION

This invention relates to fluorescence microscopy in which magnified images of tissues, cells or other components of a sample are obtained from light emission from a plurality of fluorescent dyes which can be attached to specific components or features of the sample.

High resolution imaging has and continues to play a prominent role in biology. Microscopic techniques have improved steadily in both the cellular and sub-cellular realms. Fluorescence microscopy is presently preferred because of its superior image contrast over that of conventional light scattering microscopy and because of the now well established procedure of attaching a wide variety of dyes to target related components which allows for high resolution visualization of structure-specific bindings resulting in rapid growth of an important sub-field of immunocytology.

Practical fluorescence microscopy is about fifty years old. In 1935, Max Hartinger first substituted fluorescent dyes for the then conventional stains used in histological procedures. This was developed into a routine procedure for bacteriology laboratories in the 1940's with the use of Acridine Orange as a metachromatic fluorescent stain for nucleic acids and the labeling of various proteins including specific antibodies, with isocyanate and isothiocyanate derivatives of fluorescein. Subsequently, an extensive series of other fluorescent agents, some of which are brighter and have greater avidity for specific targets, have been developed for cytological work. Technical advances such as monochromatic and epifluorescent illumination systems have reduced problems with dye bleaching and in some cases eliminated the need for barrier filters to screen out activating light.

The attractive possibility of using more than two fluorescent stains simultaneously in the same preparation, even when employing high contrast imaging techniques, has heretofore been unattainable because the spectral emission of the available dyes is typically very broad and emission in the blue range is a natural characteristic of all cells which masks or blanks out blue emitting dyes. Accordingly, only dyes that emit in the red and yellow ranges can be effectively distinguished even when employing available filtering techniques.

Use of time resolved fluorescence is an effective technique for interpreting dynamical interactions with the environment of the dye site and for obtaining information from non-single exponential decay modes. However, time resolved fluorescence has not been suggested or used for noninterfering particular spatial site selection with the exception of long decay time dyes for generalized background differentiation.

Fluorescent dyes are not the only possible site specific labels that can be used in association with present day imaging techniques. Others include shape and opacity defined labels such as latex particles, collodial gold and thorium particles, india ink, magnetite, erythrocytes and bacteria. Some of these serve purposes beyond imaging such as magnetite tagging which lends itself to separation processes and the like. In addition, there exist substrate imaging techniques such as insoluble substrate deposits and site specific alkaline etching, chemiluminescent stains and radioisotope stains which, although they provide imaging, are again limited to at most two labels simultaneously even when used in a high resolution system.

SUMMARY OF THE INVENTION

It is a primary object of the present invention to improve fluorescence microscopy.

It is therefore an object to detect a large number of fluorescent labels and stains and to view their precise spatial relationship simultaneously while eliminating nonspecific background.

A further object of the present invention is to record simultaneously from a single sample high resolution separately distinguishable correlated images from a plurality of excited dyes selected to span a large non-interferring range of decay times.

Another object of the present invention is to resolve accurately complex mixtures of micro-organisms, and the like.

Still another object of the present invention is to provide a multi-chronal fluorescence imaging technique for detecting a large number of fluorescent labels and stains which can be readily adapted to such techniques as automatic screening, time lapse photography, cinematography, computerized identification and computer translated multicolor display.

These and other objects of the present invention are attained by a multi-chronal fluorescence imaging technique for resolving simultaneously the spatial distribution of a plurality of site specific dyes while, at the same time, eliminating non specific background. The sample components are labelled by a battery of dyes that have a relatively large spread of fluorescence decay times. The stained or tagged sample components are detected and/or recorded using a high contrast imaging system.

BRIEF DESCRIPTION OF THE DRAWINGS

For a better understanding of these and other objects of the present invention reference is had to the following detailed description of the invention which is to be read in association with the following drawings, wherein.

DESCRIPTION OF THE INVENTION

Figure 1:
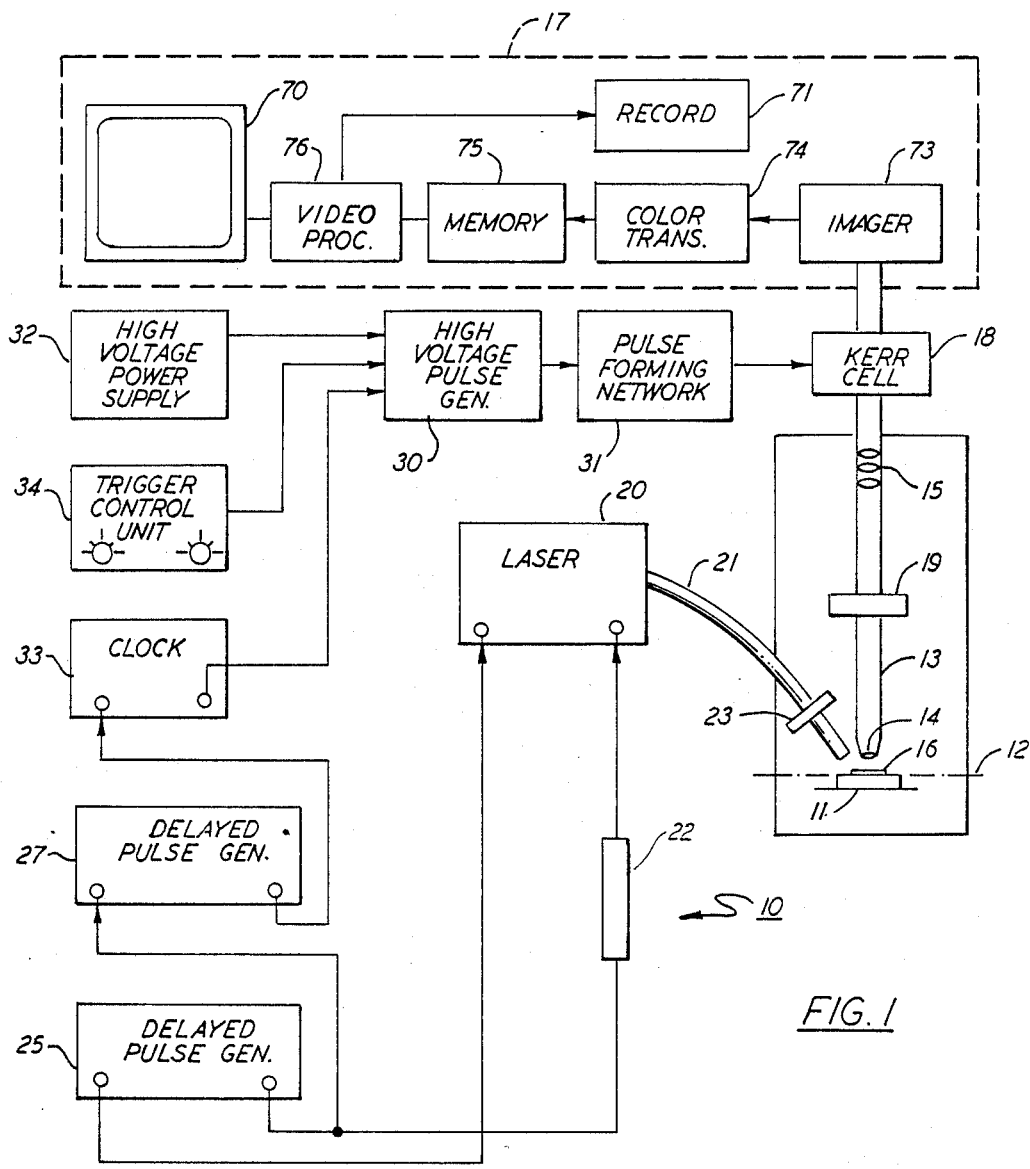
FIG. 1 is a schematic representation of a multichronal fluorescence microscope for spatially differentiating a plurality of sample components that embodies the teachings of the present invention.

Turning initially to FIG. 1, there is shown a schematic representation of a multi-chronal fluorescence microscope, generally referenced 10, which embodies the teachings of the present invention. The microscope includes a transparent sample holder 11 which is situated in the object plane 12 of a lens barrel 13. The lens barrel contains an objective lens 14 and a further lens system 15 for focusing an image of a specimen 16 in the viewing plane of an image detector 17. Positioned between the lens barrel and the detector is a gate 18 that contains an electrically actuated shutter than can be precisely opened and closed at timed intervals to permit an image of the sample to be transmitted to the detector for viewing and/or recording. A barrier filter 19 is placed in the optical path of the lens system which serves to prevent unwanted background from reaching the detector.

The sample mounted in the sample holder typically will contain different components of a biological, inorganic or organic nature to which site specific fluorescent dyes can be attached to tag or label particular sample components. Accordingly, a mixed population of cells, for example, may be stained so that particular cells in the mix will take up a fluorescent dye having a specific emission characteristic that can be easily distinguished. In the present system a plurality of dyes, each having different emission characteristics are added to the sample and are excited simultaneously by ultraviolet light from a pulsed laser 20. The light is transmitted to the sample by a flexible fiber optic bundle 21 which can be selectively positioned to direct a beam of irradiating light from above or below the transparent holder. A beam controller 23 is mounted in the bundle which can be adjusted to shape the size and intensity profile of the light beam to irradiate uniformly all or a selected portion of the sample. The traditional epifluorescent irradiation mode in which excitation light enters the sample via a dichroic mirror and through the objective lens, which in this case must be made of quartz or some other ultra-violet transmitting material, is also adaptable to our multichronal fluorescent microscope.

Preferably the ultraviolet light source 20 is a tunable dye pulsed nitrogen (N$_2$) laser that produces an output beam of radiation that is concentrated about a desired band of radiation at which the dyes readily absorb energy and become excited. A Photochemical Research Associates (PRA) low jitter nitrogen laser, Model LN 103, was used in carrying out tests on the present system and was found to operate quite well for the intended purpose. The laser is capable of producing output pulses having pulse widths of less than one nanosecond (ns), a command jitter less than two ns, and a maximum repetition rate of 100 Hz. The laser is fired in response to a pair of input trigger pulses provided by a first delayed pulse generator 25. A compensating variable delay 22 is placed in one of the input trigger lines. In practice, a Hewlett Packard generator, Model 214A having a variable delay range between 400 ns and about 10 milliseconds (ms) may be used to trigger the laser 20. As will be explained below, a second delayed pulse generator 27 of similar construction is used to trigger the gate 18 in timed relation to the firing of the laser.

As illustrated in FIG. 1, the gate 18 is connected to a high voltage pulse generator 30 by means of a pulse forming network 31. A high voltage power supply 32 is connected to that pulse generator and provides sufficient voltage to open and close the gate. A synchronous clock generator 33 is turned on by the second delayed pulse generator which applies a 1000V pulse. A trigger control unit 34 containing a thyratron acts as a fast response switch in the pulse generating network. Gate 18 is a Kerr cell manufactured by the Kappa Corporation. The cell is arranged to produce a pair of cross-polarized, electro-optical fields that can be rapidly rotated to selectively pass and block incoming light. In the present system, the cell acts as a shutter to pass light from the sample to the detector during predetermined periods of time so that the detector can view each excited dye when it is at about its maximum output intensity.

In operation, the opening and closing of the gate 18 is delayed by means of the noted second delayed pulse generator 27 until sometime after the laser has fired. As will be explained in greater detail below, sufficient time is provided after the firing of the laser to permit the sample dyes to absorb the exciting radiation and in turn begin to emit fluorescent radiation characteristic of each specific dye. The second delayed pulse generator 27 is preprogrammed to open and close the shutter at closely controlled intervals so that time resolved images produced by the dyes can be viewed or recorded simultaneously.

Although the present microscope can differentiate between seven or more dyes, its operation will be explained in regard to four specific dyes A–D which have been added to sample 16. For explanatory purposes it shall be assumed that the dyes each have equal absorptive characteristics and emission quantum efficiencies. Also for simplicity it will be further assumed that there are first order reaction kinetics and a single decay lifetime for each dye. The dyes are selected so that they exhibit relatively large differences in decay times with the decay time of each dye being separated from its faster or slower neighbor by a factor of about ten.

Figure 2:
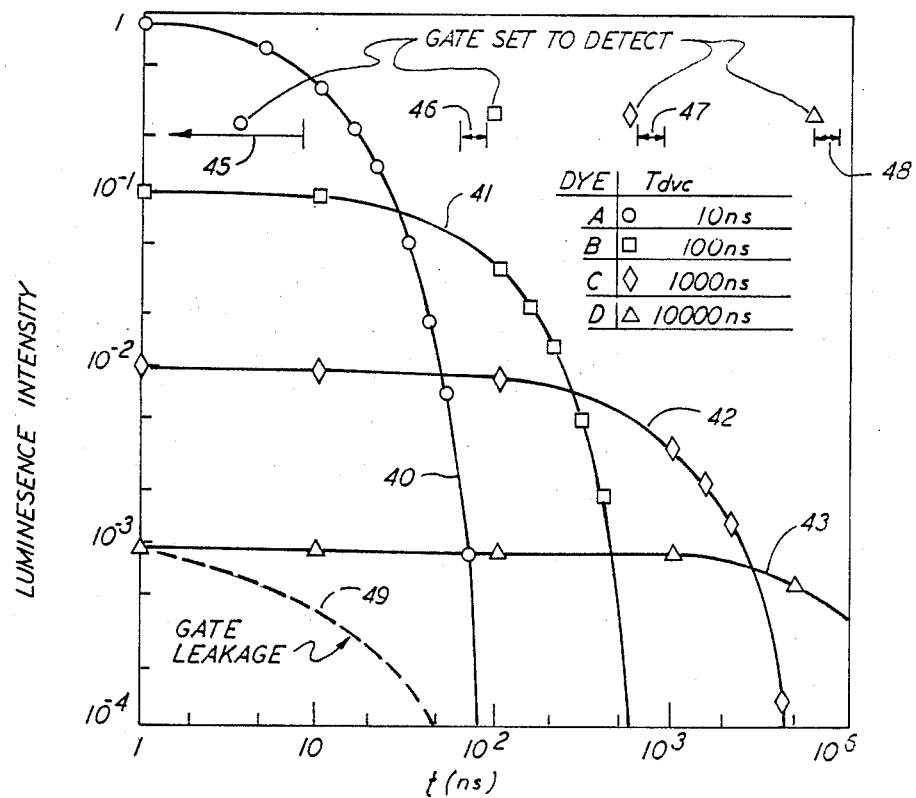
FIG. 2 is a graphic representation illustrating the delay characteristic response curves of four separate dyes after the dyes have been excited simultaneously by a pulse of irradiating light.

Turning to FIG. 2, there is shown a log-log plot illustrating the decay characteristics of the four dyes A–D after the sample has been initially irradiated with ultraviolet light. Dye A, which is represented by curve 40 reaches the highest maximum intensity output and accordingly is the first to decay. Decay to a level of about 1% its maximum intensity is reached about 46 ns after the light pulse is terminated. Dye B, as represented by curve 41, reaches a lower maximum output intensity (one-tenth that of dye A), finally decaying to its 1% maximum intensity level at about 460 ns. Similarly, dyes C and D depicted by curves 42 and 43 respectively, yield progressively lower maximum output intensities and have correspondingly longer lifetimes to reach their respective 1% maximum intensity levels, attaining these at 4.6 $\mu$s and 46 $\mu$s.

In order to observe the images produced by each of the dyes at about the dye's maximum output intensity, the shutter of the gate 18 can be programmed to open by the delayed pulse generator 27 at intervals of about 0–8 ns, 60–80 ns, 600–800 ns and 6–8 microseconds after the exciting pulse has been terminated. The gate opening interals are schematically depicted in FIG. 2 at positions 45–48. The gate is controlled so that the detector scans the irradiated sample in one of the two available modes to produce a rapid, repetitive flickering long term image of each of the dye emissions. Addition of further dyes having shorter decay times is feasible provided the gate switching circuitry is sufficiently fast to handle the increase. Use of dyes having longer decay times is also feasible, but at lower repetitive gate cycles. On-off transmission factors having a ratio of about 10 have been found satisfactory for most dye systems using up to seven dyes.

Figure 3:
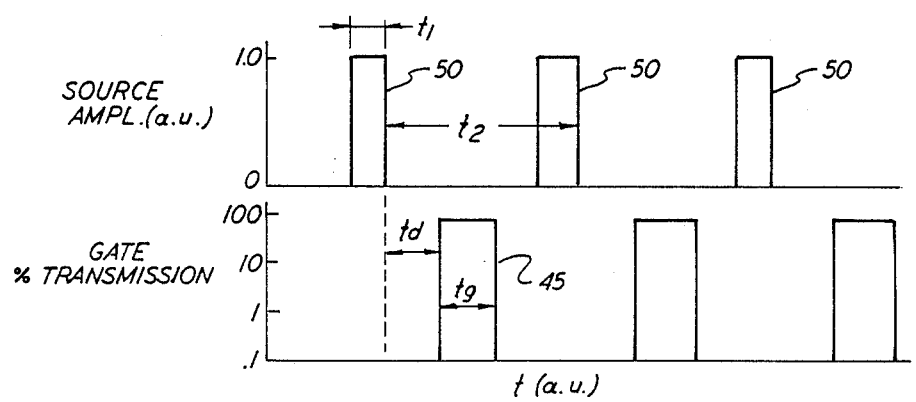
FIG. 3 is a grahic representation showing the time relationship between an irradiating pulse of light and the opening and closing of an adjustable time-resolved viewing gate to provide an image formed predominantly by one of the four dyes referred to in FIG. 2.

One contemplated scanning mode is illustrated graphically in FIG. 3. The laser is adjusted to produce a pulse 50 having a width or duration of time t. This duration is shorter than the decay time of dye A, the dye having the shortest lifetime. The delayed pulse generator 25 is further programmed to fire the laser repeatedly at timed intervals t2 which are longer than the decay time of dye D which has the longest lifetime. The gate is programmed through the second delayed pulse generator at a time delay t after the termination of each excitation pulse. In this case the system has been programmed to view an image of dye A between the first and second irradiating pulse. The gate is opened at some time earlier than 8 ns, the opening gate time being less critical for the shortest decay dye than for the others, and remains open for an interval of about 2 ns. As can be seen from FIG. 2, dye A is at about its maximum output at this time and because of its relatively high intensity the image masks that of the other dyes which are also radiating at this time. The image of dye A is thus differentiated from the other images and thus selectively viewed by the detector. The time t is the discrimination parameter for selecting which dye image will be seen by the detector. By varying the time of opening of the gate, the sample can be scanned to present images of all four dyes at the detector in an ordered sequence relating to the order in which the dye decays.

To view the emission of dye B, the time $t_d$ of opening is shifted to about 60 ns and can remain open for a period of about 20 ns. As illustrated in FIG. 2, at this time dye A has fully decayed and the intensity of dye B is now still near its peak value and predominates. As a result, the detector now sees an image produced by dye B. Similarly, the time $t_d$ can be again shifted to about 600 ns and the gate can be held open to view dye C. Finally, time $t_d$ can be moved to 6000 ns and held open for an interval of about 2000 ns to view an image of the last dye in the series which is dye D. Because of the short time intervals involved, the gate sequencing can be rapidly accomplished to produce what appears to the eye as a nonflickering steady state long term image of the output emissions of all four dyes. In this mode of operation time $t_d$ can be shifted each time the laser fires, for computer stored images, or it can be held for a large number of pulses, enough time for the eye or a camera to record the image, before being shifted. It is also contemplated that the time the gate remains open can be controlled within limits to compensate for differences in the absorptive coefficients of the dyes and/or their varying quantum efficiencies.

The example presented above is in fact a realistic one. A set of fluorescent dyes having lifetimes that differ in an ascending order by a factor of about ten might be fluorescein ($\leq 1$ ns); 3 hydroxyanthranilic acid (11 ns); pyrinobutyric acid (100 ns); unbelliferone 7-hydroxycoumarin (900 ns) and benzoquinone (200–400 $\mu$s). Many other dyes covering a large range of decay times suitable for this purpose are also known. Some examples are: toluidenylnaphthalene -6-sulfonic acid, TNS (0.6–6 ns); acrydine orange (2 ns); perylene (4.5 ns); Zinc cytochrome C (9 ns); 1-Anilino-8-naphthalene sulfonate (ANS) (15 ns); 1-Dimethylaminonaphthalene-5-sulfonic acid (DANS) (24 ns); 9-aminoacridine (28 ns); furocoumarin (50 ns); 1-pyrenebutyric acid (PBA) 102 ns; plus rhodamine B, rare earth chelates, and others.

The detector 17 (FIG. 1) can include a photographic apparatus for recording an image or series of images on film at the various selected decay times. The recorded images can be suitably registered and mapped for light intensity, translated into various easily distinguishable colors and then simultaneously displayed. A- vidicon detector or simple visual observation can also be employed. As illustrated in FIG. 1 the detector may be a video system for either displaying the images simultaneously upon a video screen 70 or recording them on a video recorder 71 for delayed playback and/or storage. Although many video systems are available one that is suitable for use in the present system includes a small camera containing a charge coupled device (CCD) capable of recording an image and converting the image data into an electrical output signal suitable for use in a standard video format. The electrical signals from the CCD imager 73 are fed through a color translator 74 to a memory 75. The images relating to the individual dyes are each color coded to more clearly differentiate visually one image from the other before the data is placed in the memory and displayed. The image signals are forwarded from the memory to a video processor 76 and then on to the video screen for viewing and/or to the recorder 71 for storage.

Figure 4:
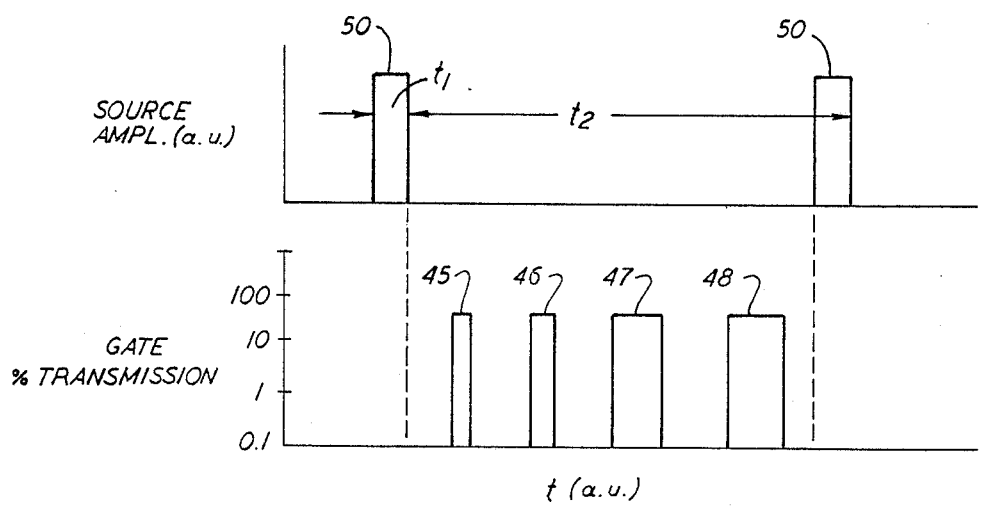
FIG. 4 is also a graphic representation similar to that shown in FIG. 3 wherein the viewing gate is opened and closed a number of times between each excitation pulse.

Turning now to FIG. 4 there is graphically illustrated a second mode of scanning in which the shutter of the gate 18 is sequentially opened and closed during period 45–48 for the time intervals noted above between each of the recurring irradiating pulses. Accordingly, an image produced by each dye is seen by the detector and is repeatedly updated between the recurring pulses. In this mode, for some dye combinations, an electrochromic color filter may be gated synchronously with the Kerr cell and placed between the Kerr cell and image detector which permits direct visual viewing of each dye image, each appearing in a color selected by the voltage applied to the electrochromic color-tunable filter.

While this invention has been described in detail with reference to the preferred embodiments hereinabove, it should be understood that the invention is certainly not limited to those embodiments, and that many modifications and variations would present themselves to those skilled in the art without departure from the scope and spirit of this invention, as defined in the appended claims.

What is claimed is:

1. A multi-chronal fluorescence imaging apparatus for spatial differentiation of a multitude of separate biological, organic and inorganic components that includes a sample holder for containing a sample with a plurality of fluorescent dyes bonded to specific sample components, said dyes each reaching a different maximum output intensity upon being excited and having substantially different decay times with the dye of greatest maximum output intensity reaching final decay first and the remaining dyes decaying in the order of their respective maximum output intensities such that the maximum output of each dye can be detected in an ordered sequence with little interference from the other dyes, a pulsed light source for periodically irradiating a sample in said holder with a pulsed excitation radiation wherein each dye emits fluorescent radiation at about its maximum output before reaching final decay.

a spatially sensitive detector means positioned in an optical light path for viewing the radiation emitted by said dyes, a gate means having a shutter movable between a closed position wherein radiation emitted by said sample is prevented from reaching the detector means and an open position wherein radiation emitted by said sample is transmitted to the detector means, means for intermittently energizing the light source to produce a light pulse having a duration that is less than the shortest decay time of said dyes, and control means to open the shutter at periodic intervals to permit the detector to view time resolved images produced by each dye prior to its decay.

2. The apparatus of claim 1 wherein said detector means further includes storage means for storing each of the dye images.

3. The apparatus of claim 2 that further includes means associated with said storage means for color translating said images and a display means for simultaneously displaying said color translated images upon a video screen.

4. The apparatus of claim 1 wherein said means for intermittently energizing the light source is arranged to repeat pulses at a rate that is slower than the slowest dye decay rate utilized.

5. The apparatus of claim 1 wherein said means for intermittently energizing the light source is arranged to repeat pulses at variable intervals to optimize the intensity of the output images of said dyes.

6. The apparatus of claim 1 wherein said light source is a laser means for producing electromagnetic radiation in a narrow wavelength band in the ultraviolet spectral region for efficiently exciting the dyes.

7. The apparatus of claim 1 that further includes a rejection filter in said light path that coacts with said shutter to reduce the intensity of the excitation pulse of the light source at the detector to a level that is lower than the detected intensity of the weakest dye.

8. The apparatus of claim 1 that further includes a beam size controller means positioned between the light source and the sample holder to control the size and uniformity of the beam used to irradiate a sample in said sampler holder.

9. The apparatus of claim 1 that further includes a fiber optics means for transmitting light from said light source to a sample in the sample holder.

10. A method of resolving spatial relations among different structural and functional components of a biological, organic and inorganic nature that includes selecting a plurality of dyes that reach different maximum output intensities upon being excited and which have substantially different decay times such that the dye of greatest maximum output intensity reaches final decay first and the remaining dyes decay in the order of their respective maximum output intensities, incorporating the dyes into a sample so that the dyes attach to components contained in the sample, illuminating the dyes in the sample with a short pulse of radiation to excite the dyes so that the dyes emit a maximum amount of radiation before decaying in an ordered sequence.

sequentially detecting the radiation emitted by the sample after the illumination pulse is terminated in a sequence corresponding to the decay sequence of the dyes to view a maximum radiation image produced by each dye before it finally decays.

11. The method of claim 10 that further includes rapidly repeating the illuminating and detecting steps to produce an apparent steady state long term image of the dye emissions.

12. The method of claim 10 that further includes the steps of positioning a gate between the sample and a detector for collecting spatial data and opening and closing the gate repeatedly after each illumination step and storing the spatial data emitted by each dye sequentially.

13. The method of claim 12 that further includes the steps of translating the stored image data from each dye to produce a separate color display for each dye, and displaying images from each of the dyes simultaneously.

14. The method of claim 10 that includes the further step of selecting the dyes so that the decay time of each successive dye in the series is about ten times longer than that of the previous dye in the series.

15. The method of claim 10 that further includes the step of selecting said dyes so that the quantum efficiency of the dyes are about equal.

16. The method of claim 12 of adjusting the duration of the gate opening cycle for each dye to compensate for small inequalities in the quantum efficiencies of the dyes.

17. The method of claim 10 that further includes the steps of placing a programmable shutter between a sample and a detector and opening the shutter at predetermined intervals and for predetermined durations after each illumination pulse.

18. The method of claim 10 that further includes the step of placing a tunable color filter between the sample and the detector that renders each radiation image visible as a separate colored image.

* * * * *